(12) United States Patent
Hoss et al.

(10) Patent No.: US 11,867,652 B2
(45) Date of Patent: Jan. 9, 2024

(54) ELECTRODES HAVING AT LEAST ONE SENSING STRUCTURE AND METHODS FOR MAKING AND USING THE SAME

(71) Applicant: Abbott Diabetes Care Inc., Alameda, CA (US)

(72) Inventors: Udo Hoss, San Ramon, CA (US); Tahir Sadik Khan, Alameda, CA (US); Phu X. Le, Dublin, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 17/682,653

(22) Filed: Feb. 28, 2022

(65) Prior Publication Data

US 2022/0276194 A1    Sep. 1, 2022

Related U.S. Application Data

(63) Continuation of application No. 16/791,058, filed on Feb. 14, 2020, now Pat. No. 11,300,537, which is a continuation of application No. 15/520,784, filed as application No. PCT/US2015/056989 on Oct. 22, 2015, now Pat. No. 10,598,624.

(60) Provisional application No. 62/067,813, filed on Oct. 23, 2014.

(51) Int. Cl.
*G01N 27/327* (2006.01)
*H01M 4/02* (2006.01)
*A61B 5/1486* (2006.01)
*G01N 27/413* (2006.01)

(52) U.S. Cl.
CPC ....... *G01N 27/3271* (2013.01); *A61B 5/1486* (2013.01); *G01N 27/413* (2013.01); *H01M 4/02* (2013.01)

(58) Field of Classification Search
None
See application file for complete search history.

(56) References Cited

U.S. PATENT DOCUMENTS

| 3,320,954 A | 5/1967 | Cowley |
| 4,953,552 A | 9/1990 | DeMarzo |
| 5,089,112 A | 2/1992 | Slotheim et al. |
| 5,165,407 A | 11/1992 | Wilson et al. |

(Continued)

FOREIGN PATENT DOCUMENTS

| EP | 1075209 B1 | 2/2001 |
| EP | 1413245 A2 | 4/2004 |

(Continued)

OTHER PUBLICATIONS

Craston, Derek H., et al., "Microband Electrodes Fabricated by Screen Printing Processes: Applications in Electroanalysis," Talania, vol. 38, No. 1, 1991, pp. 17-26.

(Continued)

*Primary Examiner* — J. Christopher Ball
*Assistant Examiner* — John C. Ball
(74) *Attorney, Agent, or Firm* — Sterne, Kessler, Goldstein & Fox P.L.L.C.

(57) ABSTRACT

An analyte sensor comprising: a non-conductive material; a conductive material disposed on the non-conductive material; and at least two sensing structures defined by a removed portion of the conductive material, the at least two sensing structures comprising a reagent composition.

18 Claims, 8 Drawing Sheets

(56) References Cited

U.S. PATENT DOCUMENTS

| | | | |
|---|---|---|---|
| 5,322,063 A | 6/1994 | Allen et al. |
| 5,390,671 A | 2/1995 | Lord et al. |
| 5,482,473 A | 1/1996 | Lord et al. |
| 5,569,186 A | 10/1996 | Lord et al. |
| 5,593,852 A | 1/1997 | Heller et al. |
| 5,660,163 A | 8/1997 | Schulman et al. |
| 5,770,028 A | 6/1998 | Maley et al. |
| 5,849,174 A | 12/1998 | Sanghera et al. |
| 5,964,993 A | 10/1999 | Blubaugh, Jr. et al. |
| 6,045,671 A | 4/2000 | Wu et al. |
| 6,093,172 A | 7/2000 | Funderburk et al. |
| 6,096,268 A | 8/2000 | Inbar |
| 6,103,033 A | 8/2000 | Say et al. |
| 6,134,461 A | 10/2000 | Say et al. |
| 6,175,752 B1 | 1/2001 | Say et al. |
| 6,198,969 B1 | 3/2001 | Kuzma |
| 6,237,394 B1 | 5/2001 | Harris et al. |
| 6,284,478 B1 | 9/2001 | Heller et al. |
| 6,336,269 B1 | 1/2002 | Eldridge et al. |
| 6,340,588 B1 | 1/2002 | Nova et al. |
| 6,424,847 B1 | 7/2002 | Mastrototaro et al. |
| 6,520,326 B2 | 2/2003 | McIvor et al. |
| 6,560,471 B1 | 5/2003 | Heller et al. |
| 6,565,509 B1 | 5/2003 | Say et al. |
| 6,579,690 B1 | 6/2003 | Bonnecaze et al. |
| 6,603,995 B1 | 8/2003 | Carter |
| 6,645,178 B1 | 11/2003 | Junker et al. |
| 6,689,056 B1 | 2/2004 | Kilcoyne et al. |
| 6,741,877 B1 | 5/2004 | Shults et al. |
| 6,746,582 B2 | 6/2004 | Heller et al. |
| 6,809,653 B1 | 10/2004 | Mann et al. |
| 6,850,859 B1 | 2/2005 | Schuh |
| 6,931,327 B2 | 8/2005 | Goode, Jr. et al. |
| 6,932,892 B2 | 8/2005 | Chen et al. |
| 6,986,756 B2 | 1/2006 | Pelkey et al. |
| 6,990,366 B2 | 1/2006 | Say et al. |
| 7,027,859 B1 | 4/2006 | McNichols et al. |
| 7,299,082 B2 | 11/2007 | Feldman et al. |
| 7,323,142 B2 | 1/2008 | Pendo et al. |
| 7,381,184 B2 | 6/2008 | Funderburk et al. |
| 7,618,369 B2 | 11/2009 | Hayter et al. |
| 7,697,967 B2 | 4/2010 | Stafford |
| 7,725,148 B2 | 5/2010 | Shah et al. |
| 7,885,698 B2 | 2/2011 | Feldman |
| 7,946,984 B2 | 5/2011 | Brister et al. |
| 7,951,080 B2 | 5/2011 | Taub |
| 8,219,173 B2 | 7/2012 | Budiman et al. |
| 8,268,143 B2 | 9/2012 | Liu et al. |
| 8,280,474 B2 | 10/2012 | Liu et al. |
| 8,323,251 B2 | 12/2012 | West et al. |
| 8,346,335 B2 | 1/2013 | Harper et al. |
| 9,241,631 B2 | 1/2016 | Valdes et al. |
| 9,504,471 B2 | 11/2016 | Vaitekunas et al. |
| 9,668,682 B2 | 6/2017 | Brister et al. |
| 9,788,766 B2 | 10/2017 | Simpson et al. |
| 9,808,574 B2 | 11/2017 | Yodfat et al. |
| 10,820,842 B2 | 11/2020 | Harper |
| 10,827,954 B2 | 11/2020 | Hoss et al. |
| 10,874,338 B2 | 12/2020 | Stafford |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 11,000,213 B2 | 5/2021 | Kamath et al. |
| 11,000,216 B2 | 5/2021 | Curry et al. |
| 11,013,440 B2 | 5/2021 | Lee et al. |
| 11,064,917 B2 | 7/2021 | Simpson et al. |
| 11,141,084 B2 | 10/2021 | Funderburk et al. |
| 2001/0020546 A1 | 9/2001 | Eldridge et al. |
| 2002/0119711 A1 | 8/2002 | VanAntwerp et al. |
| 2002/0161288 A1 | 10/2002 | Shin et al. |
| 2002/0169369 A1 | 11/2002 | Ward et al. |
| 2003/0042137 A1 | 3/2003 | Mao et al. |
| 2003/0097082 A1 | 5/2003 | Purdy et al. |
| 2003/0100040 A1 | 5/2003 | Bonnecaze et al. |
| 2003/0144581 A1 | 7/2003 | Conn et al. |
| 2003/0153900 A1 | 8/2003 | Aceti et al. |
| 2003/0225361 A1 | 12/2003 | Sabra |
| 2004/0061232 A1 | 4/2004 | Shah et al. |
| 2004/0106860 A1 | 6/2004 | Say et al. |
| 2004/0133164 A1 | 7/2004 | Funderburk et al. |
| 2004/0178066 A1* | 9/2004 | Miyazaki ......... G01N 33/48771 |
| | | 204/403.01 |
| 2005/0027181 A1 | 2/2005 | Goode, Jr. et al. |
| 2005/0038332 A1 | 2/2005 | Saidara et al. |
| 2005/0192557 A1 | 9/2005 | Brauker et al. |
| 2005/0215871 A1 | 9/2005 | Feldman et al. |
| 2005/0239154 A1 | 10/2005 | Feldman et al. |
| 2005/0242479 A1 | 11/2005 | Petisce et al. |
| 2005/0245799 A1 | 11/2005 | Brauker et al. |
| 2005/0261563 A1 | 11/2005 | Zhou et al. |
| 2006/0001550 A1 | 1/2006 | Mann et al. |
| 2006/0016700 A1 | 1/2006 | Brister et al. |
| 2006/0019327 A1 | 1/2006 | Brister et al. |
| 2006/0020187 A1 | 1/2006 | Brister et al. |
| 2006/0094944 A1 | 5/2006 | Chuang |
| 2006/0142651 A1 | 6/2006 | Brister et al. |
| 2006/0178625 A1 | 8/2006 | Lim et al. |
| 2006/0257996 A1 | 11/2006 | Simpson et al. |
| 2006/0258959 A1 | 11/2006 | Sode |
| 2007/0135774 A1 | 6/2007 | Turner et al. |
| 2008/0059133 A1 | 3/2008 | Edwards et al. |
| 2008/0161666 A1 | 7/2008 | Feldman et al. |
| 2008/0172205 A1 | 7/2008 | Breton et al. |
| 2009/0054748 A1 | 2/2009 | Feldman |
| 2009/0065357 A1* | 3/2009 | Glezer ................. B01L 3/5027 |
| | | 204/403.01 |
| 2009/0076360 A1 | 3/2009 | Brister et al. |
| 2009/0102678 A1 | 4/2009 | Mazza et al. |
| 2009/0178459 A1 | 7/2009 | Li et al. |
| 2009/0247857 A1* | 10/2009 | Harper ................. A61B 5/1486 |
| | | 600/365 |
| 2009/0299301 A1 | 12/2009 | Gottlieb et al. |
| 2010/0081909 A1 | 4/2010 | Budiman et al. |
| 2010/0094110 A1* | 4/2010 | Heller ................. A61B 5/4848 |
| | | 600/345 |
| 2010/0145377 A1 | 6/2010 | Lai et al. |
| 2010/0230285 A1 | 9/2010 | Hoss et al. |
| 2012/0197098 A1 | 8/2012 | Donnay et al. |
| 2013/0150691 A1 | 6/2013 | Pace et al. |
| 2015/0005601 A1 | 1/2015 | Hoss et al. |

FOREIGN PATENT DOCUMENTS

| | | |
|---|---|---|
| EP | 2407094 A1 | 1/2012 |
| GB | 2067764 A | 7/1981 |
| WO | WO 98/56293 A1 | 12/1998 |
| WO | WO 99/56613 A1 | 11/1999 |
| WO | WO 99/58190 A1 | 11/1999 |
| WO | WO 00/49942 A1 | 8/2000 |
| WO | WO 01/52727 A1 | 7/2001 |
| WO | WO 01/58348 A2 | 8/2001 |
| WO | WO 01/64105 A1 | 9/2001 |
| WO | WO 02/15778 A1 | 2/2002 |
| WO | WO 02/058537 A2 | 8/2002 |
| WO | WO 03/056319 A2 | 7/2003 |
| WO | WO 2004/088275 A2 | 10/2004 |
| WO | WO 2005/011779 A1 | 2/2005 |
| WO | WO 2005/018450 A2 | 3/2005 |
| WO | WO 2005/041766 A1 | 5/2005 |
| WO | WO 2005/065542 A2 | 7/2005 |
| WO | WO 2006/018447 A2 | 2/2006 |
| WO | WO 2006/040083 A1 | 4/2006 |
| WO | WO 2006/094513 A2 | 9/2006 |
| WO | WO 2007/097754 A1 | 8/2007 |
| WO | WO 2009/066288 A1 | 5/2009 |

(56) References Cited

OTHER PUBLICATIONS

"Abbott's Continuous Blood Glucose Monitor Approval Soon," press release dated Oct. 3, 2006; 3 pages; available at: https://www.diabetesincontrol.com/.
"Diabetes Close Up," DCU Conferences—#2, Diabetes Technology, Nov. 2003; 8 pages; available at: http://www.closeconcerns.com.
"Diabetes, Abstract Book" Journal of the American Diabetes Association, vol. 53, Suppl. 2, Jun. 2004; 12 pages.
"Freestyle Navigator Continuous Glucose Monitoring System, User's Guide," Section 1, Abbott, 2010; 38 pages.
Abbott Diabetes Care, Inc., "Premarket Approval Application Amendment, FreeStyle Navigator Continuous Glucose Monitoring System," vol. 2, Section III, Device Description, May 11, 2006; 89 pages.
Chen, Ting et al., "Defining the Period of Recovery of the Glucose Concentration after Its Local Perturbation by the Implantation of a Miniature Sensor," Clin Chem Lab Med, 40(8), 2002; pp. 786-789.
Cunningham, David D. and Stenken, Julia A., Editors, "In Vivo Glucose Sensing," Chemical Analysis, vol. 174, Chapter 1, John Wiley & Sons, Inc., Hoboken, NJ 2010; 27 pages.
Dexcom Inc., "Leading the Way for You & Your Patients with Continuous Glucose Monitoring," 2010; 12 pages.
Dexcom, Inc., Form 10-K, 2005; 59 pages; available at: http://www.sec.gov.
FDA—PMA database search for Freestyle Navigator Continuous Glucose Monitor, accessed Jan. 2022; available at—https://www.fda.gov; 6 pages.
Feldman, Ben, Ph.D., "A Continuous Glucose Sensor Based on Wired Enzyme™ Technology—Results from a 3-Day Trial in Patients with Type 1 Diabetes," Diabetes Tech. & Therapeutics, vol. 5, No. 5, 2003; pp. 769-779.
Heller, Adam and Feldman, Ben, "Electrochemical Glucose Sensors and Their Applications in Diabetes Management," Chem. Rev., No. 108, 2008; pp. 2482-2505.
Heller, Adam and Feldman, Ben, "Electrochemistry in Diabetes Management," Accounts of Chemical Research, vol. 43, No. 7, Jul. 2010; pp. 963-973.
Heller, Adam, "Integrated Medical Feedback Systems for Drug Delivery," AIChE Journal, vol. 51, No. 4, Apr. 2005; pp. 1054-1066.
Medtronic MiniMed, "Guardian RT Continuous Glucose Monitoring System REF MMT-7900," User Guide, 2005; 128 pages.
Medtronic MiniMed, "Guardian Real-Time Continuous Glucose Monitoring System," User Guide, 2006; 181 pages.
TheraSense, Inc., "Original Premarket Approval Application for FreeStyle Navigator Continuous Glucose Monitoring System, Section VII Manufacturing Section, Steven Label Sensor Sheet Validation Plan," vol. 28, Jun. 7, 2005; 61 pages.
Ward, M.D. Kenneth W. et al., "A Wire-Based Dual-Analyte Sensor for Glucose and Lactate: In Vitro and In Vivo Evaluation," Diabetes, Tech. & Therapeutics, vol. 6, No. 3, 2004; pp. 389-401.
"2nd International Conference on Advanced Technologies & Treatments for Diabetes," Kenes International, Feb. 25-28, 2009; 4 pages.
Bruckel, J. et al., "In Vivo Measurement of Subcutaneous Glucose Concentrations with an Enzymatic Glucose Sensor and a Wick Method," Klin Wochenschr (1989) 67:491-495.
Chen, T.L., and You, R.Z., "A novel fault-tolerant sensor system for sensor drift compensation," Elsevier, vol. 147, Issue 2, Oct. 3, 2008, pp. 623-632.
"Cleo™ 90 Infusion Set, Summary of Safety and Effectiveness," Smiths Medical MD, Inc., Aug. 10, 2004; 618 pages.
FreeStyle Navigator, Continuous Glucose Monitoring System, User Guide, Abbott Diabetes Care, Inc., 2008; 195 pages.
Gerritsen, M. et al., "Performance of subcutaneously implanted glucose sensors for continuous monitoring," The Netherlands Journal of Medicine, vol. 54, 1999; pp. 167-179.
Hoss, Udo et al. "Continuous Glucose Monitoring in the Tissue: Do We Really Need to Calibrate In-Vivo?" Abbott Diabetes Care, 2009; 23 pages.
Hoss, Udo, Ph.D et al., "Continuous Glucose Monitoring in Subcutaneous Tissue Using Factory-Calibrated Sensors: A Pilot Study," Diabetes Technology & Therapeutics, vol. 12, No. 8, 2010; 8 pages.
Hoss, Udo, Ph.D et al., "Feasibility of Factory Calibration for Subcutaneous Glucose Sensors in Subjects with Diabetes," Journal of Diabetes Science and Technology, vol. 8 (1), 2014, pp. 89-94.
Insulet 019 UST400 User Manual, Insulet Corp., 2011; 190 pages.
Kalivas, J.H. and Kowalski, B.R., "Compensation for Drift and Interferences in Multicomponent Analysis," Office of Naval Research, Technical Report No. 21, Jan. 1982; 38 pages.
Lau, John H. and Barrett, George E., "Stress and Deflection Analysis of Partially Routed Panels for Depanelization," IEEE Transactions on Components, Hybrids, and Manufacturing Technology, vol. CHMT-10, No. 3, Sep. 1987, 9 pages.
Letter from Department of Health and Human Services to Abbott Diabetes Care, Inc. Re PMA approval for Freestyle Navigator Continuous Glucose Monitoring System, Mar. 12, 2008; 7 pages (Exhibit 19).
Mastrototaro, John J. et al., "An Electroenzymatic Glucose Sensor Fabricated on a Flexible Substrate," Sensors and Actuators B, 5 (1991); pp. 139-144.
Medtronic MiniMed, "Paradigm Real-Time-522 and 722 Insulin Pumps," User Guide, 2008 (Excerpts) 25 pages.
Tegnestedt, C. et al., "Levels and sources of sound in the intensive care unit—An observational study of three room types," Acta Anaesthesiol Scand 2013; 11 pages.
Thevenot, Daniel R. et al., "Electrochemical Biosensors: Recommended Definitions and Classification," Pure Appl. Chem. vol. 71, No. 12, 1999; pp. 2333-2348.
Walt, David R. and Agayn, Venetka I., "The Chemistry of enzyme and protein immobilization with glutaraldehyde," Trends in Analytical Chemistry, vol. 13, No. 10, 1994; 6 pages.
Watkin, Jared, "An Introduction to Flash Glucose Monitoring," Abbott Diabetes Care, 2013; 16 pages.
Zhang, Yanan, Ph.D., "Investigations of Potentially Implantable Glucose Sensors," University of Kansas, 1991; 24 pages.

\* cited by examiner

ELECTRODES HAVING AT LEAST ONE SENSING STRUCTURE AND METHODS FOR MAKING AND USING THE SAME

CROSS-REFERENCE TO RELATED APPLICATION

This application is a continuation of U.S. application Ser. No. 16/791,058, filed Feb. 14, 2020, which application is a continuation of U.S. application Ser. No. 15/520,784, filed Apr. 20, 2017, which claims the benefit of PCT/US2015/056989, filed Oct. 22, 2015, which claims priority based on U.S. Provisional Application No. 62/067,813, filed Oct. 23, 2014, the disclosures of which are incorporated herein by reference in their entireties.

INTRODUCTION

In many instances it is desirable to regularly monitor the concentration of particular analytes in body fluid of a subject. A number of systems are available that analyze an analyte in a bodily fluid, such as blood, plasma, serum, interstitial fluid, urine, tears, and saliva. Such systems monitor the level of particular medically relevant analytes, such as, blood sugars, e.g., glucose, cholesterol, ketones, vitamins, proteins, and various metabolites.

In vivo analyte monitoring systems that automatically monitor analyte level include an in vivo positioned analyte sensor. At least a portion of the sensor is positioned beneath the skin surface of a user to contact bodily fluid (e.g., blood or interstitial fluid (ISF)) to monitor one or more analytes in the fluid over a period of time.

While automatic glucose monitoring is desirable, there are several challenges associated with manufacturing sensing elements of biosensors constructed for in vivo use. Accordingly, further development of improved analyte sensors having a higher degree of accuracy as well as reduced sensor-to-sensor variation is desirable.

SUMMARY

Embodiments of the present disclosure relate to electrochemical analyte sensor electrodes that have one or more sensing structures, each structure has a respective perimeter at least partially around it to define the structure so that each of the structures have a liquid-limiting barrier that surrounds them. A liquid-limiting perimeter may completely or partially encompass the perimeter of each sensing structure of an electrode. Also provided are methods for fabricating the electrodes, analyte sensors employing the subject electrodes, and methods of using the analyte sensors in analyte monitoring.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

DETAILED DESCRIPTION

Figure 1:
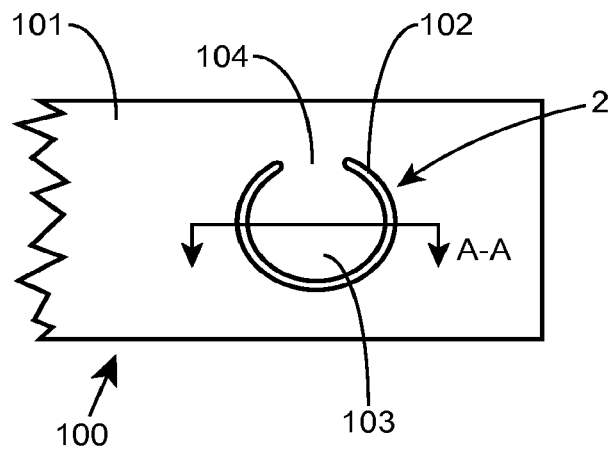
FIG. 1 shows a schematic of an electrode with a sensing structure with an incomplete fluid barrier perimeter having a single discontinuity or opening.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be embodied by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

Electrodes having at Least One Bounded Sensing Structure

Aspects of the present disclosure include electrochemical analyte sensors having an electrode such as a working electrode. An electrode includes at least one, and in many embodiments a plurality of, individualized or spaced apart conductive sensing structures (see for example sensing structures 2, 12, 22 of FIGS. 1, 2, 3, respectively). An electrode may be planar or non-planar and may be any suitable size, as desired, having a length which ranges from 0.1 mm to 5.0 mm, such as from 0.5 mm to 4.5 mm, such as from 1.0 mm to 4.0 mm, such as from 1.5 mm to 3.0 mm and including 2.5 mm and a width which ranges from 0.1 mm to 5.0 mm, such as from 0.5 mm to 4.5 mm, such as from 1.0 mm to 4.0 mm, such as from 1.5 mm to 3.0 mm and including 2.5 mm. It is understood, however that shorter or longer lengths and narrower or wider widths may also suitable. The geometric area of the electrode may range from 0.01 $mm^2$ to 25.0 $mm^2$, such as from 0.1 $mm^2$ to 20.0 $mm^2$, such as from 1.0 $mm^2$ to 15.0 $mm^2$, such as from 1.0 $mm^2$ to 10 $mm^2$ and including 5.0 $mm^2$.

The sensing structures are each delimited by a fluid barrier perimeter. The perimeter of a sensing structure retains applied analyte sensing solution, such as analyte responsive enzyme, within its boundaries while the solution dries during the manufacturing processes. As a result, the diameter of each sensing structure is controlled to avoid potentially unwanted spread of the applied solution during the drying process. This allows for manufacturing of electrodes with uniform diameters for each sensing structure of a given electrode and between different electrodes, resulting in very little to no sensing structure variation of a given electrode and between different electrodes of the same or different analyte sensor, and little to no electrode-to-electrode variation of the same or different analyte sensor. This little to no sensing structure-to-sensing structure variation and electrode-to-electrode variation provides analyte sensors manufactured with these electrodes with little to no variation in detecting analyte amounts, and higher accuracy as compared to sensors that do not have the sensing structures disclosed herein. Analyte sensors manufactured with these electrodes therefore are factory-only calibration sensors in that they do not need calibration during their in vivo wear (i.e., use) period and they maintain high accuracy and reliability solely from calibration during the manufacturing process, in other words they do not need user calibration from an in vitro reference point such as an in vitro blood glucose test strip or other reference standard after manufacture.

Figure 2:
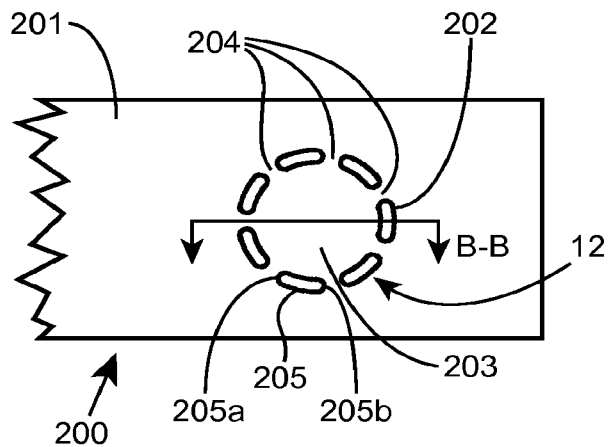
FIG. 2 shows a schematic of an electrode with a sensing structure with an incomplete fluid barrier perimeter having a plurality of discontinuities or openings.

In some embodiments, a sensing structure includes an incomplete or discontinuous fluid barrier perimeter as exemplified by sensing structures 2 and 12 in FIG. 1 and FIG. 2, respectively. In other embodiments, a sensing structure includes a complete fluid barrier perimeter completely surrounding (e.g., encircling) each sensing structure as exemplified by sensing structure 22 in FIG. 3. A fluid barrier perimeter may be an absence or removal of at least a portion of conductive material defining the electrode (see for example structures 102, 202, and 302 of electrodes 100, 200, 300, respectively). A perimeter may be a conductive material-removed area in that conductive material is removed from a larger conductive area so that an underlying conductive or non-conductive material is thereby exposed. The height of a fluid barrier perimeter may differ from the height of the interior sensing area that it surrounds. Perimeter barriers may be embossed, scribed, etched or ablated barriers, such by use of a laser. In instances where the fluid barrier perimeter is incomplete, the incomplete perimeter of each sensing structure has at least one area that does not have conductive material removed so that at least one break in the perimeter is present (see for example breaks 104, 204 of FIGS. 1 and 2, respectively).

It will also be appreciated by one having skill in the art that such a fluid retaining barrier may also be formed by addition of a retaining barrier, such as a build-up of material, such as by application of additional material to the surface of the electrode to form a wall-like structure to form the sensing structures. The additional material may the same material as the materiel used to form the electrode or may be a different material and may be applied to the surface of the electrode in a variety of well knows methods, including for example, surface deposition, printing, as well as positioning and immobilizing of pre-formed elements on the surface of the electrode, such as a gasket.

The sensing structures may be any suitable shape, as desired, such as in the shape of a triangle, square, rectangle, circle, ellipse, or other regular or irregular polygonal shape (e.g., when viewed from above) as well as other two-dimensional shapes such as a circle, half circle or crescent shape. The overall width (e.g., diameter in embodiments in which the sensing structure is generally circular) of each sensing structure formed within the electrode area may be no less than 0.001 mm and no greater than 1.0 mm. For example, the length may be between 0.005 mm and 0.9 mm, such as 0.01 mm to 0.8 mm, such as 0.1 mm to 0.7 mm and including 0.25 mm to 0.5 mm. Shorter and longer sensing structures may also suitable. In certain embodiments, the overall width of each sensing structure formed within the electrode area may be no less than 0.001 mm and no greater than 1.0 mm. For example, the length may be between 0.005 mm and 0.9 mm, such as 0.01 mm to 0.8 mm, such as 0.1 mm to 0.7 mm and including 0.25 mm to 0.5 mm. The area of each sensing structure within the electrode structure ranges from 0.0001 $mm^2$ to 1.25 $mm^2$, such as from 0.001 mm² to 1.0 mm², such as from 0.001 mm² to 0.9 mm², such as from 0.01 mm² to 0.75 mm² and including from 0.1 mm² to 0.5 mm².

FIG. 1 shows an embodiment of an electrode 100 that has a sensing structure 2. Structure 2 includes a fluid-limiting perimeter 102 that has an opening 104, i.e., it is discontinuous, and an interior region within the boundaries of the perimeter 103.

FIG. 2 shows another embodiment of an electrode 200 that has a sensing structure 12. Structure 12 includes a plurality of discontinuities or openings 204. Therefore this embodiment includes a perimeter that has seven sections 205 separated by seven spaces 204, and each section has two disconnected ends 205a, 205b, all of which encircle the interior portion 203. Stated otherwise, at least some ends of the sections of a perimeter do not touch any other sections.

Figure 3:
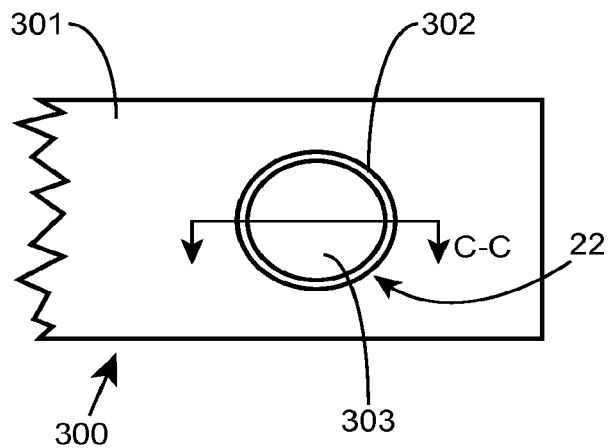
FIG. 3 shows a schematic of an electrode with a sensing structure with a fluid barrier perimeter completely surrounding the sensing structure.

FIG. 3 shows an embodiment of an electrode 300 that has a sensing structure 22 that has a perimeter 302 that is complete, i.e., has no discontinuities, and completely encircles the interior 303.

Figure 4A:
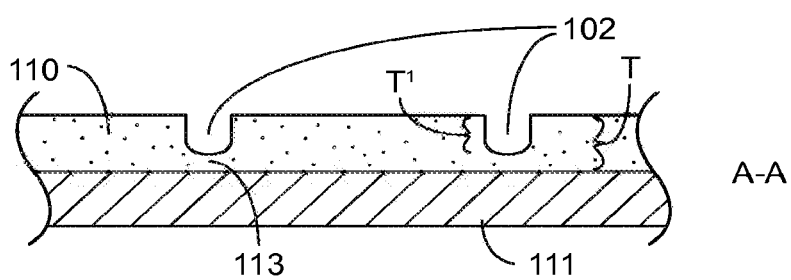
FIGS. 4A-4C show a series of exemplary cross-sections at point A-A of the fluid retaining barrier of FIG. 1.
Figure 4B:
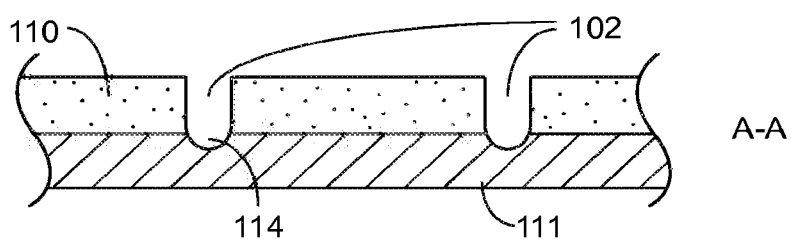
Figure 4C:
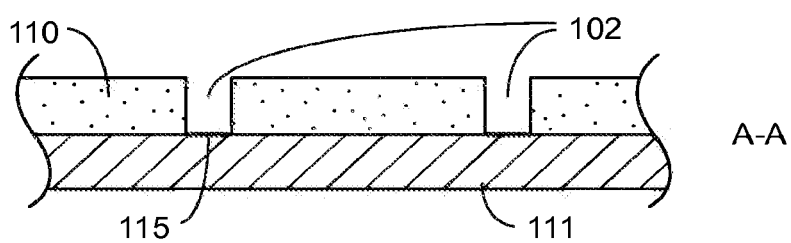
Figure 5A:
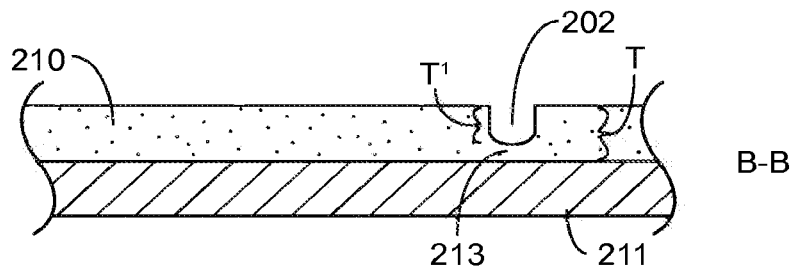
FIGS. 5A-5C show a series of exemplary cross-sections at point B-B of the fluid retaining barrier of FIG. 2.
Figure 5B:
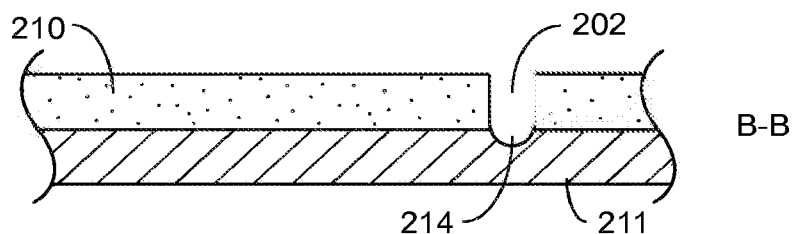
Figure 5C:
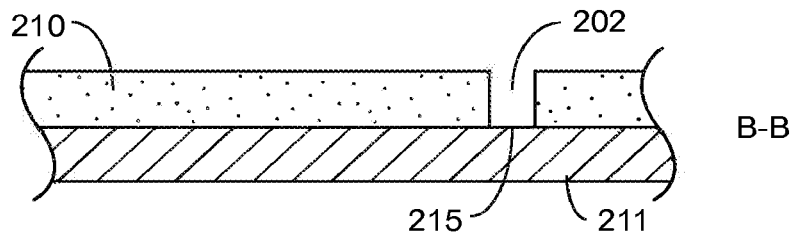

Schematic cross-sections of the exemplary fluid retaining barriers and sensing structures of FIG. 1 and FIG. 2 are shown in FIGS. 4A-4C and FIGS. 5A-5C, respectively. FIGS. 4A and 5A show conductive layer 110, 210, having a thickness T, and a non-conductive material layer 111, 211. In these embodiments, only a portion $T^1$ of the conductive layer is removed (i.e., less than thickness T) at the fluid barrier perimeter 102, 202, thereby providing a conductive material remainder portion 113, 213 on the non-conductive material 111, 211 that has a thickness that is less than the total or original conductive material thickness T. FIGS. 4B and 5B show embodiments in which the entirety of the thickness T of conductive layer 110, 210 as well as a portion 114, 214 of the non-conductive material portion 111, 211 is removed at the fluid barrier perimeter 102, 202. FIGS. 4C and 5C depict an embodiment in which the entirety of the thickness T of conductive layer 110, 210 is removed at the fluid barrier perimeter 102, 202, but not into the conductive material, leaving a surface 115, 215 of the conductive material 110, 210 exposed.

The depth of a perimeter may range from 1 µm to 25 µm, such as from 2 µm to 22.5 µm, such as from 3 µm to 20 µm, such as from 4 µm to 17.5 µm, such as from 5 µm to 15 µm and including from 10 µm to 15 µm. For example, in some embodiments the depth of the perimeter is 10 µm.

It should be appreciated that whether the perimeter of each sensing structure is incomplete or complete, the region within the boundaries of the perimeter 103, 203, 303, i.e., the sensing structure, remains in electrical communication with the region outside of the boundaries of the perimeter 101, 201, 301. In embodiments in which the fluid barrier perimeter is incomplete, the portion(s) of the perimeter not defined by the absence or removal of a portion of conductive material 104, 204 may provide the electrical communication between the regions within 103, 203 and outside 101, 201 of the fluid barrier perimeter.

Figure 6:
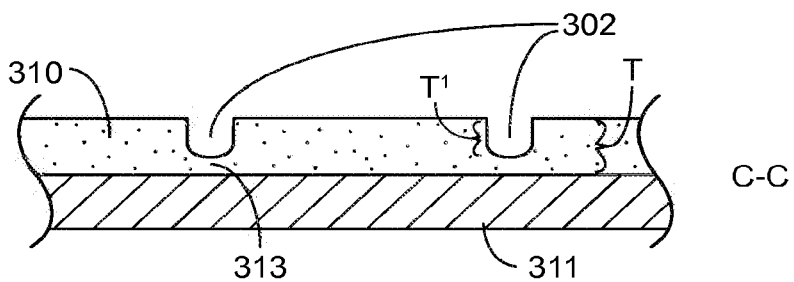
FIG. 6 shows an exemplary cross-section at point C-C of the fluid retaining barrier of FIG. 3.

In embodiments in which the fluid barrier perimeter includes a complete fluid barrier perimeter surrounding (e.g., encircling) each sensing structure as exemplified in FIG. 3, electrical communication between the regions within 303 and outside 301 of the fluid barrier perimeter may be provided by only removing a portion of the conductive layer. A schematic cross-section exemplifying a fluid retaining barrier that maintains electrical communication between the regions within 303 and outside 301 of the fluid barrier perimeter of FIG. 3 is shown in FIG. 6. FIG. 6 depicts an embodiment in which only a portion of the conductive layer 310 is removed at the fluid barrier perimeter 302, thereby providing a conductive material remainder portion 313. In these embodiments, conductive layer 310 has a thickness T and only a portion $T^1$ of the conductive layer is removed (i.e., less than thickness T) at the fluid barrier perimeter 302 thereby providing a conductive material remainder portion 313 on the non-conductive material 311 that has a thickness that is less than the total or original conductive material thickness T. The portion of the conductive material disposed on the material may provide the electrical communication between the regions within 303 and outside of the fluid barrier perimeter of FIG. 3.

As described, an electrode includes at least one non-conductive material, with at least one conductive material. Suitable non-conductive materials may include, but are not limited to, polymeric, plastic, glass, silicon-containing materials, dielectric materials, or ceramic materials, among other non-conductive materials. In some embodiments, the material is a flexible, deformable or thermoplastic material of polycarbonate, polyester (e.g., polyethylene terephthalate (PET)), polyvinyl chloride (PVC), polyurethane, polyether, polyamide, polyimide, combinations or copolymers thereof, such as glycol-modified polyethylene terephthalate. In other embodiments, the non-conductive material may be a rigid material such as aluminum oxide and silicon dioxide. A material may also have a varying rigidity along a dimension of the material. In certain embodiments, the non-conductive material is a porous or microporous material. For example, the material may be formed, for example, as a mesh, a reticulated structure (e.g., reticulated graphite), a microporous film, or a film that is permeable to an analyte of interest. Other examples of suitable material s may include those described in U.S. Pat. No. 6,175,752, the disclosure of which is herein incorporated by reference.

The thickness of the non-conductive material may vary, depending on the applied conductive layer protocol (e.g., laser ablation, scribing, or etching) for defining the electrode structure or forming the perimeter of each sensing structure within the electrode structure. For example, the material may have a thickness of 25 µm or more, such as 50 µm or more, such as 100 µm or more, such as 150 µm or more, such as 200 µm or more, such as 300 µm. For example, the thickness of the material may range from 1 µm to 300 µm, such as from 10 µm to 250 µm, such as from 50 µm to 200 µm, such as 100 µm to 150 µm and including from 10 µm to 200 µm.

In some cases, the non-conductive material is roughened to have a textured surface. The textured surface may have a cross-sectional profile that includes one or more local maxima and/or local minima (i.e., peaks and valleys). The textured surface may have a regular, repeated arrangement of peaks and valleys, or in some instances, may have in irregular, random distribution of peaks and valleys across the surface of the non-conductive material. For example, the non-conductive material may have a systematic arrangement of peaks and valleys, such that a majority of the peaks have the same height and a majority of the valleys have the same depth. In some instances, the peaks may have an average height of 1 mm or less, such as 0.5 mm or less, including 0.25 mm or less, or 0.1 mm or less, or 0.05 mm or less, such as 0.01 mm or less, or 0.001 mm or less. In certain cases, the valleys may have an average depth of 1 mm or less, such as 0.5 mm or less, including 0.25 mm or less, or 0.1 mm or less, or 0.05 mm or less, such as 0.01 mm or less, or 0.001 mm or less. In one example, the textured material surface is configured to increase adhesion of the conductive layer to the non-conductive material such that adhesion is greater or improved for a textured surface than for a non-textured surface. In another example, the textured non-conductive material surface is configured to at least minimize, including eliminate, cracking of the applied conductive layer. In yet another example, the textured non-conductive material surface is configured to prevent, include eliminate, corrosion of the conductive layer when applying electric potentials to the electrode. In still another example, the textured surface is an adhesion promoter that promotes sufficient adhesion between the conductive layer and the non-conductive material without the need for an adhesion layer (e.g., chromium) between the non-conductive material and the conductive layer.

In certain embodiments, the non-conductive material having a textured surface has an increased coefficient of friction as compared to a material that does not include a textured surface. In some cases, the textured surface has a coefficient of friction of 0.1 or more, such as 0.2 or more, or 0.3 or more, or 0.4 or more, including 0.5 or more, or 0.6 or more, such as 0.7 or more, or 0.8 or more, for instance 0.9 or more, or 1 or more, or 1.1 or more, or 1.2 or more, or 1.3 or more, including 1.4 or more, or 1.5 or more, or 1.6 or more, such as 1.7 or more, or 1.8 or more, or 1.9 or more, for example 2 or more.

As discussed above, conductive material is applied to the surface of a non-conductive material to form a conductive layer, either directly or indirectly. The composition of the conductive layer deposited onto the surface of the non-conductive material may vary depending on the conductive properties desired. The conductive layer may include but is not limited to, conductive polymers, carbon (e.g., graphite), metals, alloys (e.g., gold, silver, titanium, platinum or any alloy thereof), or a metallic oxide composition (e.g., indium tin oxide (ITO) ruthenium dioxide or titanium dioxide). For example, the composition of the conductive layer may include but is not limited to conductive polymer, aluminum, carbon (e.g., graphite), cobalt, copper, gallium, gold, indium, iridium, iron, lead, magnesium, mercury (as an amalgam), nickel, niobium, osmium, palladium, platinum, platinum-carbon, rhenium, rhodium, selenium, silicon (e.g., doped polycrystalline silicon), silver, tantalum, tin, titanium, tungsten, uranium, vanadium, zinc, zirconium, mixtures thereof; and alloys, oxides, or metallic compounds of these elements, for example indium tin oxide (ITO). In certain instances, the composition of the conductive layer is gold (Au).

The conductive layer may include one or more of the aforementioned materials. For example, the conductive layer may include two or more components, such as three or more components, such as four or more components, including five or more components. In certain embodiments, the conductive layer consists of only a single component. In these embodiments, the composition of the conductive layer contains a pure composition of one component, as described in greater detail below. By "pure" is meant that the composition of the conductive layer contains 99.5% or greater of a single material, such as 99.9% or greater, such as 99.99% or greater, such as 99.998% or greater of a single material. As such, the conductive layer includes 0.5% or less of any impurity, such as 0.1% or less, such as 0.05% or less, such as 0.01% or less, such as 0.005% or less, including 0.002% or less of any impurity.

The thickness of the conductive layer may range from 1 µm to 300 µm or more, such as from 10 µm to 250 µm, such as from 50 µm to 200 µm, such as 100 µm to 150 µm and including from 10 µm to 200 µm. In certain embodiments the thickness of the conductive layer may be 25 µm, 50 µm, 100 µm, 150 µm, 200 µm, 300 µm, or more.

The conductive layer may cover all or part of a surface of the non-conductive base upon which the electrode is defined. In some embodiments, the conductive layer covers part of the surface of non-conductive material, such as 50% or more of the surface, such as 55% or more, such as 60% or more, such as 65% or more, such as 75% or more, such as 90% or more, such as 95% or more and including 99% or more of the surface of the non-conductive material. In certain embodiments, the conductive layer covers the entire surface of the non-conductive material. The conductive layer may also be applied to more than one surface of the non-conductive material. In some embodiments, conductive layer is applied to only one surface of the non-conductive material. In other embodiments, the conductive layer is applied to two or more surfaces of the non-conductive material, such as three or more surfaces of the non-conductive material, such as four or more surfaces of the non-conductive material and including five or more surfaces of the non-conductive material. In certain embodiments, the conductive layer is applied to all surfaces of the non-conductive material.

Figure 7:
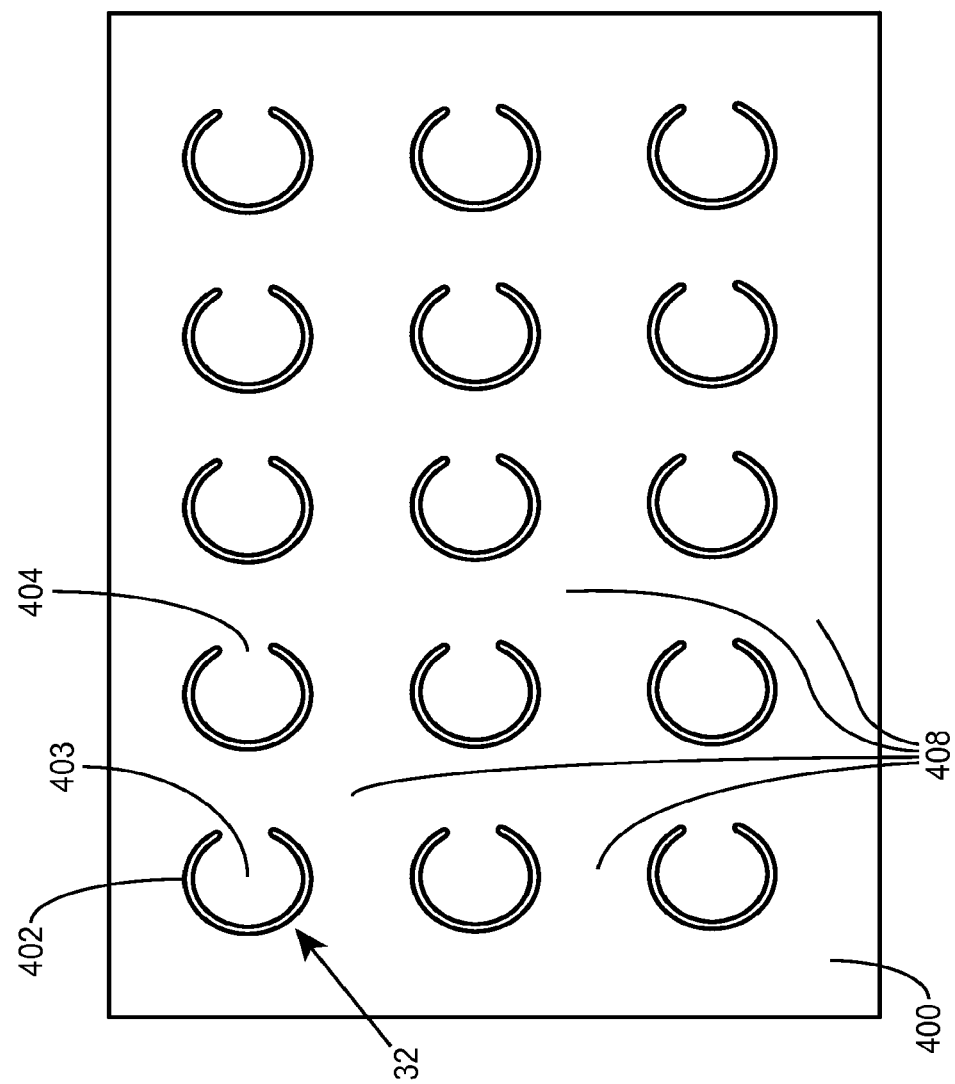
FIG. 7 shows a schematic view of an electrode having a plurality of sensing structure with an incomplete fluid barrier perimeter having a single of discontinuity or opening.
Figure 8:
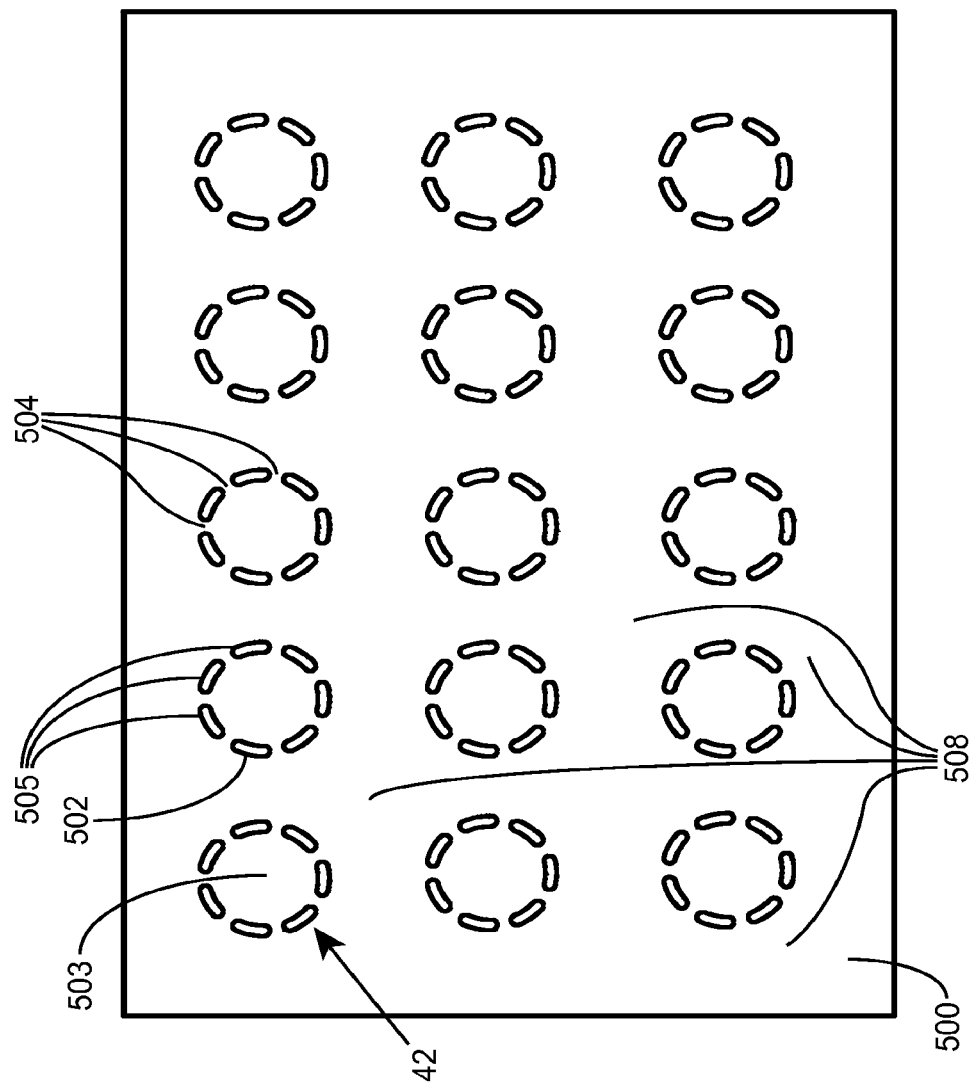
FIG. 8 shows a schematic view of an electrode having a plurality of sensing structure with an incomplete fluid barrier perimeter having a plurality of discontinuities or openings.

Two or more sensing structures may be provided on a working electrode. These may be in a uniform pattern or grid, for example disposed laterally to each other as shown in FIGS. 7 and 8, or in a non-uniform or irregular pattern. The number and pattern/location of sensing structures shown are exemplary only, and fewer or more can be used. For example, there can be a single structure, or at least two in a single row of structures along an axis such as a longitudinal axis of an electrode. All or less than all can include reagent composition, which may be the same or different. Arrays of sensing structures with incomplete perimeters are shown schematically in FIGS. 7 and 8. FIG. 7 shows an embodiment in which the working electrode 400 includes a grid of sensing structures 32 having incomplete perimeters 402 formed from a single removed portion of conductive material so that there is a single opening 404 in the perimeters that encompasses the interiors 403. FIG. 8 shows an embodiment in which the electrode 500 includes an array of sensing structures 42 having incomplete perimeters 502 formed from a plurality of removed portions 504 of conductive material to form detached sections 505 of the perimeter that encompasses the interiors 503.

Any given electrode may include one, two, four or more arrays of sensing structures. Depending upon the use, any or all of the arrays may be the same or different from one another. For example, an array may include 2 or more, 5 or more, 10 or more, 25 or more, 50 or more, 100 or more features, or even 1000 or more features, in an area of 100 mm$^2$ or less, such as 75 mm$^2$ or less, or 50 mm$^2$ or less, for instance 25 mm$^2$ or less, or 10 mm$^2$ or less, or 5 mm$^2$ or less, such as 2 mm$^2$ or less, or 1 mm$^2$ or less, 0.5 mm$^2$ or less, or 0.1 mm$^2$ or less.

In certain embodiments, the electrode includes areas between the one or more sensing structures, referred to as inter-sensing structure areas. Exemplary inter-sensing structure areas 408 and 508 are shown for example in FIGS. 7 and 8. As such, in some instances, the inter-sensing structure areas do not include (e.g., are free of) reagent composition, such as an analyte-responsive enzyme. In addition, in some cases, the inter-sensing structure areas do not include (e.g., arc free of) a redox mediator or polymer bound, covalently or non-covalently, redox mediator. The inter-sensing structure areas may surround the sensing structures as exemplified in FIGS. 7 and 8, such that, as described herein, the sensing structures are in close proximity and not adjoined to one another. In some cases, the distance between adjacent sensing structures (e.g., the inter-sensing structure areas distance) may be 0.1 µm or more, 0.5 µm or more, 1 µm or more, such as 10 µm or more, including 50 µm or more, or 100 µm or more, or 150 µm or more, or 200 µm or more, or 250 µm or more, for instance 500 µm or more. The inter-feature distance may range from 0.1 µm to 500 µm, or from 0.5 µm to 500 µm, or from 1 µm to 500 µm, such as from 1 µm to 250 µm, including from 5 µm to 200 µm, for instance from 10 µm to 200 µm. Inter-feature areas, when present, could be of various sizes and configurations.

In embodiments of the present disclosure, analyte-responsive enzyme is distributed throughout the deposited reagent composition confined to the interior of one or more sensing structures. For example, analyte-responsive enzyme may be distributed uniformly throughout the deposited reagent composition, such that the concentration of the analyte-responsive enzyme is the same throughout the deposited reagent composition. In some cases, deposited reagent composition may have a homogeneous distribution of the analyte-responsive enzyme. In certain embodiments, deposited reagent further includes a redox mediator that is distributed throughout the deposited reagent composition. For example, the redox mediator may be distributed uniformly throughout the deposited reagent composition, such that the concentration of the redox mediator is the same throughout the deposited reagent composition. In some cases, deposited reagent composition has a homogeneous distribution of the redox mediator. In certain embodiments, both analyte-responsive enzyme and redox mediator are distributed uniformly throughout the deposited reagent composition.

Depending on the size of each of the one or more sensing structures, the amount of deposited reagent composition may vary, so long as the deposited reagent composition does not exceed an amount which can be confined within the boundaries of the sensing structure by the fluid barrier perimeter and may range from 0.01 to 1000 nanoliters (nL), such as from 0.1 to 750 nL, including from 1 to 500 nL, or from 1 to 250 nL, or from 1 to 100 nL, for instance from 1 to 75 nL, or from 1 to 50 nL, such as from 1 to 25 nL, or from 1 to 10 nL, for example from 1 to 5 nL. In certain embodiments, the amount of reagent composition deposited in each sensing structure may range from 1 to 50 nL.

The thickness of the layer of deposited reagent composition within each sensing structure will depend on the amount of reagent composition deposited. In some embodiments, one or more layers of the reagent composition is deposited, such as two or more layers, such as three or more layers, such as five or more layers, and including ten or more layers of the reagent composition are applied to the material. Accordingly, the total thickness of the deposited reagent composition may be 0.1 nm or more, such as 0.5 nm or more, such as 1.0 nm or more, such as 1.5 nm or more, such as 2.0 nm or more, such as 5 nm or more, such as 10 nm or more, including 100 nm or more. Additional layers of the reagent composition may be added if necessary, such as for example to improve smoothness and uniformity.

In some embodiments, the reagent composition deposited in each sensing structure has an arcuate profile. In certain cases, the deposited reagent composition has a shape approximating that of a half sphere, where the rounded semi-spherical portion of the deposited reagent composition is convex and extends a distance above the surface of the material (e.g., the surface of the electrode).

In those embodiments in which a perimeter includes one discontinuity as exemplified in FIGS. 1, 2, 7, 8, i.e., it is an incomplete or discontinuous perimeter, it may be 50% or more of a complete perimeter, such as 55% or more, such as 60% or more, such as 65% or more, such as 70% or more, such as 75% or more, such as 80% or more, such as 85% or more, such as 90% or more and including an 95% or more of a complete perimeter. Depending on the size of each sensing structure, the incomplete perimeter formed around each sensing structure, i.e., the distance 104, 204, 404, 504 of FIGS. 1, 2, 7 and 8, respectively, between two leading, spaced apart ends of a perimeter, may be incomplete by 500 µm or less, such as 450 µm or less, such as 400 µm or less, such as 350 µm or less, such as 300 µm or less, such as 250 µm or less, such as 200 µm or less, such as 150 µm or less and including by 100 µm or less.

As mentioned above, a variety of sensing structure shapes may be used, and in some embodiments one electrode may include more than one shape. In certain embodiments, a perimeter is in the shape of a circle, or partial circle if the perimeter is incomplete. In circle or other embodiments, the incomplete perimeter may be in the form of a circle which is 99% or less complete, such as a 95% or less complete, such as 90% or less complete, such as 85% or less complete, such as 80% or less complete, such as 75% or less complete, such as 70% or less complete, such as 65% or less complete, such as 60% or less complete, such as 55% or less complete and including an incomplete perimeter in the form of a circle which is 50% or less complete. For example, the incomplete perimeter may include 320° or more of a circle, such as 325° or more of a circle, such as 330° or more of a circle, such as 335° or more of a circle, such as 340° or more of a circle, such as 345° or more of a circle and including 350° or more of a circle. In other instances, the perimeter around each circular sensing structure may be incomplete by 500 µm or less, such as 450 µm or less, such as 400 µm or less, such as 350 µm or less, such as 300 µm or less, such as 250 µm or less, such as 200 µm or less, such as 150 µm or less and including a boundary around each sensing structure which is incomplete by 100 µm or less.

In some cases, an incomplete perimeter around each sensing structure includes more than one discontinuity as exemplified in FIGS. 2 and 8. For instance, an incomplete sensing structure perimeter may be a set of portions of removed conductive layer, such as a series of dots or lines which collectively form the incomplete perimeter. Discontiguous incomplete perimeters may include 2 or more portions, such as 3 or more portions, such as 4 or more portions, such as 5 or more portions, such as 10 or more portions, such as 25 or more portions and including 50 or more portions. In other embodiments, the incomplete perimeter is a single removed portion of conductive layer which forms the shape of the incomplete perimeter as exemplified in FIGS. 1 and 7.

A mass transport limiting layer (not shown), e.g., an analyte flux modulating layer, may also be included to act as a diffusion-limiting barrier to reduce the rate of mass transport of the analyte, for example, glucose or lactate, when the sensor is in use. The mass transport limiting layers limit the flux of an analyte to the electrode in an electrochemical sensor so that the sensor is linearly responsive over a large range of analyte concentrations. Mass transport limiting layers may include polymers and may be biocompatible. A mass transport limiting layer may provide many functions, e.g., biocompatibility and/or interferent-eliminating functions, etc., or functions may be provided by various membrane layers.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over the reagent composition-containing sensing structures and allowing the solution to cure for about one to two days or other appropriate time period. The crosslinker-polymer solution may be applied over the sensing elements by placing a droplet or droplets of the membrane solution on the sensor, by dipping the sensor into the membrane solution, by spraying the membrane solution on the sensor, and the like. Generally, the thickness of the membrane is controlled by the concentration of the membrane solution, by the number of droplets of the membrane solution applied, by the number of times the sensor is dipped in the membrane solution, by the volume of membrane solution sprayed on the sensor, or by any combination of these factors. A membrane applied in this manner may have any combination of the following functions: (1) mass transport limitation, i.e., reduction of the flux of analyte that can reach the sensing elements, (2) biocompatibility enhancement, or (3) interferent reduction.

In some instances, the membrane may form one or more bonds with the sensing elements. By bonds is meant any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the membrane can form crosslinks between the polymers of the membrane and the polymers in the sensing elements. In certain embodiments, crosslinking of the membrane to the sensing element facilitates a reduction in the occurrence of delamination of the membrane from the sensor.

In certain embodiments, the electrode is part of a sensing system which detects hydrogen peroxide to infer glucose levels. For example, a hydrogen peroxide-detecting sensor may be constructed in which the reagent composition includes an enzyme such as glucose oxidase, glucose dehydrogenase, or the like, and is positioned on a working electrode. The reagent composition may be covered by one or more layers, e.g., a membrane that is selectively permeable to glucose. Once the glucose passes through the membrane, it is oxidized by the enzyme and reduced glucose oxidase can then be oxidized by reacting with molecular oxygen to produce hydrogen peroxide.

Methods of Fabricating an Electrode Having One or More Sensing Structures with Fluid Barrier Perimeters As summarized above, aspects of the present disclosure include methods for fabricating an electrode for use in an electrochemical sensor that has at least one defined sensing structure. Embodiments include forming an electrode and at least one sensing structure with the electrode, and applying a composition to the interior of the at least one sensing structure to bound it within the structure. Some embodiments include applying a conductive layer to the surface of a non-conductive material, removing a portion of the conductive layer to define an electrode on the surface of the material, removing at least a portion in the conductive layer within the boundary of the electrode to form a sensing structure having an incomplete perimeter around the sensing structure and depositing a chemical reagent having an analyte responsive enzyme within the boundaries of the sensing structure of the electrode.

In fabricating the subject electrodes, a reagent composition is contacted with the conductive layer surface of one or more of the sensing electrode structures, forming a deposition of the reagent composition within the incomplete perimeter of each sensing structure. During the deposition process, the applied reagent composition fills the sensing structure and is stopped from migrating on the conductive layer surface of the electrode beyond or outside of the incomplete perimeter. Without being limited to any particular theory, in certain instances, by restricting migration of the reagent composition during deposition, the reagent composition is more uniformly distributed (e.g., the center of the deposited drop of reagent composition has the same thickness as the edges) as compared to a reagent deposited in the absence of an incomplete perimeter around the sensing structure. In some embodiments, the uniformly distributed reagent composition deposited reduces or eliminates variation in sensitivity of the electrode in an electrochemical sensor.

In practicing methods according to certain embodiments, a conductive material is applied to the surface of a non-conductive material, as described above, to form a conductive layer. The term "applying" is used herein in its conventional sense to refer to placing one or more materials onto a surface, such as for example onto the surface of a material. As such, applying may include positioning on top, depositing or otherwise producing a material (e.g., conductive or nonconductive) on a surface. In embodiments of the present disclosure, applying includes depositing a layer of conductive material onto one or more surfaces of a non-conductive material. For example, methods may include depositing a thin layer of conductive material onto a surface, such as layer having a thickness of 1 μm or more, such as 2 μm or more, such as 5 μm or more, such as 10 μm or more, such as 25 μm or more, such as 50 μm or more, such as 100 μm or more, such as 150 μm or more, such as 200 μm or more, such as 300 μm. For example, the conductive layer may range from 1 μm to 300 μm, such as from 10 μm to 250 μm, such as from 50 μm to 200 μm, such as 100 μm to 150 μm and including from 10 μm to 200 μm. In certain instances, methods include depositing a layer of conductive material having a thickness of 180 μm. In embodiments, conductive material may be applied over the entire surface or a part of the surface of the non-conductive material, as desired. In some embodiments, applying conductive material to a surface includes depositing conductive material onto 50% or more of the surface, such as 55% or more, such as 60% or more, such as 65% or more, such as 75% or more and including 90% or more of the surface. In certain instances, methods include depositing a layer of conductive material onto the entire surface of the material. Where the non-conductive material is planar, the conductive layer may be applied to one or more surfaces of the non-conductive material. In some embodiments, conductive layer is applied to one surface of the non-conductive material. In other embodiments, the conductive layer is applied to two or more surfaces of the non-conductive material, such as 3 or more surfaces of the non-conductive material, such as 4 or more surfaces of the non-conductive material and including 5 or more surfaces of the non-conductive material. In certain embodiments, the conductive layer is applied to up to all six surfaces of the non-conductive material.

The conductive layer, as described above, may be applied onto the non-conductive material using any suitable technology, e.g., chemical vapor deposition (CVD), physical vapor deposition, sputtering, reactive sputtering, printing, coating, painting, dip coating, etching, electron beam thermal evaporation, among other deposition methodologies.

As discussed above, methods according to embodiments of the present disclosure may optionally include removing a portion of the conductive layer to define one or more electrodes on the surface of the material. By "removing a portion of the conductive layer to define one or more electrodes" is meant that a predetermined part of the conductive layer is taken away from the applied conductive layer to form isolated areas having the desired configuration and dimensions of an electrode. Any suitable subtractive process may be employed to remove a portion of the conductive layer to define the one or more electrodes. In certain embodiments, the boundaries defining the electrode structure on the non-conductive material are fabricated by laser ablation to trim and ablate away conductive material. The term "laser ablation" is used herein in its conventional sense to refer to the process of removing material from a surface using a laser having a beam profile with dimensions that are smaller than the feature size of the formed pattern.

In certain embodiments, laser ablation may include the use of a mask, pattern or other device intermediate between the laser source and the conductive layer to define a pattern in which portions of the laser beam impinge on the conductive layer to define a pattern of an electrode in the conductive layer. In other embodiments, no mask, pattern or other device is positioned between the laser source and the conductive layer and the pattern ablated by the laser are produced by simply guiding the laser along a path of the pattern desired.

In fabricating the subject electrodes, methods also include removing at least a portion of the conductive layer within the defined electrode and form a sensing structure having an incomplete perimeter of exposed non-conductive material surface around the sensing structure. The removal of conductive material may result in portion of the conductive material to remain at the location of removal (see for example FIGS. 4A, 5A and 6), the conductive material may be completely removed (see for example FIGS. 4C and 5C), or the conductive material may be completely removed as well as portion of the material (see for example FIGS. 4B and 5B).

Any suitable subtractive process may be employed to form isolated areas having an incomplete perimeter around the desired configuration and dimensions of sensing structures within the electrode. In certain embodiments, removing at least a portion of the conductive layer to define the sensing structures with incomplete perimeters includes laser ablation. Laser ablation to form the sensing structures with incomplete perimeters may include the use of a mask, pattern or other device intermediate between the laser source and the conductive layer to define the desired pattern of the sensing structure. The same or different laser ablation protocol may be employed to remove a portion of the conductive layer to define the sensing structure within the electrode as used to define the electrode.

Any suitable laser ablation protocol may be employed to remove at least a portion of the conductive layer to define an electrode, so long as it removes the desired amount of the conductive material impinged by the laser beam profile along the desired path. For example, a suitable laser ablation protocol may include, but is not limited to, that described in United States Patent Application Publication No. 2010/0230285, the disclosure of which is herein incorporated by reference.

In certain embodiments, the removing at least a portion of the conductive layer to form incomplete perimeters around one or more sensing structures within the electrode may include laser ablating through the conductive layer to a predetermined depth that is less than the thickness of the conductive material, such that a portion of the conductive material remains along the desired path. As such, an incomplete perimeter forms a depression into the conductive material but does not expose the underlying non-conductive material (see for example FIGS. 4A, 5A and 6).

In other embodiments, the removing at least a portion of the conductive layer to form incomplete perimeters around one or more sensing structures within the electrode may include laser ablating through the conductive layer to a predetermined depth into the non-conductive material (see for example FIGS. 4B and 5B). As such, the incomplete perimeter forms a depression into the non-conductive material. The depression into the non-conductive material is defined by a bottom surface and side walls. The bottom surface of the depression into the non-conductive material is lower in height than the surface of the non-conductive material surrounding the depression, such that the depression extends a certain depth below the surface of the non-conductive material surrounding the depression. In some instances, the depression into the non-conductive material has a curved bottom surface, such that the depression has a concave cross-sectional profile. In certain cases, the depression into the non-conductive material has a flat (e.g., planar) bottom surface.

In some embodiments, the one or more sensing structures within the electrodes are fabricated concurrently while fabricating the electrode. Where laser ablation is employed to remove a portion of the conductive layer to define the electrode and to form incomplete perimeters around the one or more sensing structures within the electrode, the portion of the conductive layer to define the electrode is removed simultaneously while removing the portion of the conductive layer to form incomplete perimeters around the one or more sensing structures within the electrode. Laser ablation to remove conductive layer to define the electrode and to remove conductive layer to form incomplete perimeters around the one or more sensing structures within the electrode may include one or more lasers, as necessary, such as two or more lasers and including three or more lasers. In certain embodiments, a single laser is used to ablate the conductive layer to simultaneously remove conductive layer material to define the electrode and to remove conductive layer to form incomplete perimeters around the one or more sensing structures within the electrode.

In other embodiments, the electrode and incomplete perimeters around the one or more sensing structures are fabricated sequentially. In other words, methods according to these embodiments include first removing a portion of the conductive layer to define the electrode followed by removing a portion of the conductive layer to form incomplete perimeters around the one or more sensing structures within the electrodes. The incomplete perimeters around the one or more sensing structures may be prepared immediately after fabricating the electrode or may be preparing at a predetermined after fabricating the electrode, such as 1 minute or more after preparing the electrode, such as 2 minutes or more, such as 5 minutes or more, such as 10 minutes or more, such as 15 minutes or more, such as 30 minutes or more, such as 60 minutes or more and including 120 minutes or more after preparing the electrode.

The subject electrodes may include one, two, four or more arrays of sensing structures. Depending upon use, any or all of the arrays may be the same or different from one another. For example, an array may include two or more, 5 or more, ten or more, 25 or more, 50 or more, 100 or more features, or even 1000 or more features, in an area of 100 mm$^2$ or less, such as 75 mm$^2$ or less, or 50 mm$^2$ or less, for instance 25 mm$^2$ or less, or 10 mm$^2$ or less, or 5 mm$^2$ or less, such as 2 mm$^2$ or less, or 1 mm$^2$ or less, 0.5 mm$^2$ or less, or 0.1 mm$^2$ or less.

Methods also include depositing a reagent composition on the sensing structure of the electrode. As described in greater detail above, the reagent composition includes an analyte responsive enzyme, such as a glucose responsive enzyme (e.g., glucose oxidase, glucose dehydrogenase, etc.) or lactate responsive enzyme (e.g., lactate oxidase) and in some embodiments, also includes a redox mediator, such as a hydrogen peroxide or a transition metal complex. As discussed above, each of the one or more sensing structures includes an incomplete perimeter such that deposited reagent composition remains generally confined within the sensing structure.

The reagent composition may be deposited by any non-impact or impact printing method, such as for example, from a pulse-jet device. A "pulse-jet" is a device that can dispense drops in the formation of an array. Pulse-jet devices operate by delivering a pulse of pressure to liquid adjacent an outlet or orifice such that a drop will be dispensed therefrom (for example, by a piezoelectric or thermoelectric element positioned in the same chamber as the orifice). In certain embodiments, the drops may be dispensed using a dispenser device configured to operate similar to an inkjet printing device, as described above. In certain embodiments, the pulse jet device includes a dispensing head configured to dispense drops, such as, but not limited to, sensing layer formulation, in the formation of an array. The dispensing head may include one or more deposition chambers for containing the formulation(s) to be deposited. The amount of fluid that is deposited in a single activation event of a pulse jet can be controlled by changing one or more of a number of parameters, including the size of the orifice in the dispensing head (e.g., the orifice diameter), the size of the deposition chamber, the size of the piezoelectric or thermoelectric element, etc.

The reagent composition may be deposited on the surface of the electrode following formation of the sensing structures on the electrode, or alternatively, the reagent composition may be deposited on the electrode surface first, followed by forming of the incomplete perimeters around the deposited reagent composition to form the sensing structures on the electrode. For example, in some embodiments, methods include initially depositing the reagent composition on a sensing structure of the electrode and subsequently removing a portion of the conductive layer to form an incomplete perimeter around the deposited reagent composition. In these embodiments, methods include the steps of applying a conductive material to a surface of a material to form a conductive layer, removing a portion of the conductive layer to define an electrode on the surface of the material, depositing a reagent comprising an analyte responsive enzyme on a structure of the electrode, and removing a portion of the conductive layer to form an incomplete perimeter around the deposited reagent composition.

Removing a portion of conductive layer to form incomplete perimeters around the one or more deposited reagent compositions may be carried out according the same methods described above for embodiments in which the reagent is deposited after the incomplete perimeter is formed.

Moreover, it will be appreciated that depending on the shape of the deposited reagent composition, the incomplete perimeter formed around each deposited reagent may vary. For example, in certain embodiments, the deposited reagent is circular and the incomplete perimeter is an incomplete circle. In other embodiments, the shape will be of a triangle, square, rectangle, circle, ellipse, or other regular or irregular polygonal shape (e.g., when viewed from above) as well as other two-dimensional shapes such as a circle, half circle or crescent shape.

Fabricating an electrode according to embodiments of the present disclosure produces a reproducible reagent composition deposited on the surface of the electrode. The term "reproducible" is used herein in its conventional sense to mean that the deposited reagent compositions on the electrodes are substantially identical showing little to no deviation, such as in parameters including but not limited to size, shape, thickness, mechanical strength, hardness, transparency and distribution of components throughout the deposited composition. For example, sensing layers described herein may deviate from each other by 5% or less, such as by 4% or less, such as by 3% or less, such as by 2% or less, such as by 1% or less and including by 0.5% or less. In certain embodiments, deposited reagent compositions show no deviation from one another and are substantially identical.

In certain embodiments, deposition of the reagent composition into sensing structures having an incomplete perimeter around each sensing structure results in a reduction, and in some cases, complete elimination of the "coffee ring" effect. Without being limited to any particular theory, in certain instances, during the drying, the constituents of the reagent composition migrate towards the outer edges of the deposition due to a faster rate of evaporation at the thinner peripheral edges of the deposition. This results in a greater concentration of the constituents of the solution at the peripheral edges of the deposition, resulting in a so-called "coffee ring" effect. Analyte sensors are traditionally manufactured by depositing a stripe or relatively large drop of a sensing layer formulation onto the surface of an electrode, which, in some cases, may result in a "coffee ring" effect as described above. For example, as described above, when an elongated stripe of sensing layer formulation dries on the surface of the electrode, constituents in the sensing layer formulation may migrate towards the outer edges of the stripe, resulting in an uneven coating of the sensing layer formulation on the surface of the electrode with a higher concentration of the sensing layer formulation near the edges of the sensing layer stripe.

In certain embodiments, methods further include drying the reagent composition deposited on the sensing structures of the electrode. Drying may be performed at room temperature, at an elevated temperature, as desired, such as at a temperature ranging from 25° C. to 100° C., such as from 30° C. to 80° C. and including from 40° C. to 60° C.

In some embodiments, prior to applying the conductive layer, the non-conductive material surface is conditioned for applying the conductive layer. By "conditioned" is meant that the non-conductive material surface is processed or otherwise prepares the non-conductive material surface to be more receptive to the applied conductive layer such that conditioning the non-conductive material surface improves the mechanical robustness of the applied conductive layer as compared to a conductive layer applied to a non-conductive material which has not be conditioned according to the subject methods. In certain embodiments, conditioning the non-conductive material surface includes roughening the surface of the non-conductive material. By "roughening" is meant producing a textured material surface. A textured surface includes surfaces that are not smooth surfaces. The non-conductive material may be roughened by any suitable protocol, including but not limited to a physical process (e.g., laser machining, sand blasting, etching, imprinting processes) or a chemical process (e.g., chemical etching)

In some instances, the conductive layer may be applied to the material immediately after conditioning (e.g., roughening) the non-conductive material. In other instances, the conductive layer is deposited onto the non-conductive material a predetermined period after conditioning (e.g., roughening) the non-conductive material. For example, the conductive layer may be applied to the material, 1 second or more after conditioning, such as 2 seconds or more, such as 5 seconds or more, such as 10 seconds or more, such as 60 seconds or more, including 100 seconds or more after conditioning the non-conductive material. In certain instances, the treated material may be stored for a period of time before applying the conductive layer to the material. In certain instances, the material may be stored for 1 to 1000 days or longer, such as 1 to 100 days or longer, including 1 to 10 days or longer. Any storage method may be employed so long as it is sufficient to store the conditioned material without changing any of the desired properties of the material. For example, the conditioned material may be stored under reduced pressure, such as at a pressure of $10^{-2}$ torr or lower, such as $10^{-3}$, such as $10^{-4}$ torr or lower, such as $10^{-5}$ torr or lower, such as $10^{-6}$ torr or lower, such as $10^{-7}$ torr or lower, including $10^{-8}$ torr or lower. In other instances, the conditioned material may be stored in an unreactive gas sample. The term "unreactive gas sample" is used in its conventional sense to refer to a gaseous atmosphere which does not result in any type of chemical interaction with the conditioned material. For example, the conditioned material may be stored under a $N_2$ or argon gaseous atmosphere.

In one example, if after assessing that the texture of the non-conductive material is sufficiently roughened, the conductive layer may be applied to the non-conductive material without further adjustment. However, if after assessing that the texture of the non-conductive material is not sufficiently roughened or is not homogeneously roughened, the non-conductive material may be further processed until the texture is suitable for application of the conductive layer. In another example, if after assessing that the applied conductive layer is suitable for laser ablation to define the electrode structure and/or form an incomplete perimeter around each sensing structure within the electrode structure, the laser beam for ablation may be impinged on the applied conductive layer without any further adjustments. Alternatively, if after assessing that the applied conductive layer is unsuitable for laser ablation to define the electrode structure, one or more adjustments to the conductive layer may be made, such as reducing or increasing the thickness of the conductive layer or improving the uniformity of the applied conductive layer, etc. If necessary, each fabrication step may be altered one or more times during methods of the present disclosure.

Electrochemical Analyte Sensors

Aspects of the present disclosure also include an analyte sensor employing one or more of the subject electrodes described above. In embodiments, the analyte sensor includes: a working electrode; and a counter electrode where the working electrode includes a non-conductive material; a conductive layer disposed on and in contact with the material and a sensing structure on the conductive layer having an incomplete perimeter around the sensing structure and reagent, such as analyte responsive enzyme, positioned within the boundaries of the sensing structure.

The particular configuration of electrochemical sensors may depend on the use for which the electrochemical sensor is intended and the conditions under which the electrochemical sensor will operate. In certain embodiments of the present disclosure, electrochemical sensors are in vivo wholly positioned electrochemical analyte sensors or transcutaneously positioned electrochemical analyte sensors configured for in vivo positioning in a subject. For example, at least a portion of an in vivo sensor may be positioned in the subcutaneous tissue for testing analyte concentrations in interstitial fluid.

A variety of analytes can be monitored in the body of a subject using the analyte sensors disclosed herein including, but not limited to, glucose, oxygen, pH, carbon dioxide, chloride, potassium, electrolytes, ketones, lactate, pyruvate, of body fluid. In certain embodiments, the analyte sensors of the present disclosure are glucose sensors.

Examples of suitable in vivo electrochemical analyte sensors and methods for making them which may include one or more electrodes as described herein include, but are not limited to, those described in U.S. Pat. Nos. 6,175,752, 6,134,461, 6,579,690, 6,605,200, 6,605,201, 6,654,625, 6,746,582, 6,932,894, 7,090,756, 5,356,786, 6,560,471, 5,262,035, 6,881,551, 6,121,009, 6,071,391, 6,377,894, 6,600,997, 6,514,460, 5,820,551, 6,736,957, 6,503,381, 6,676,816, 6,514,718, 5,593,852, 6,284,478, 7,299,082, 7,811,231, 7,822,557 8,106,780, and 8,435,682; U.S. Patent Application Publication Nos. 2010/0198034, 2010/0324392, 2010/0326842, 2007/0095661, 2010/0213057, 2011/0120865, 2011/0124994, 2011/0124993, 2010/0213057, 2011/0213225, 2011/0126188, 2011/0256024, 2011/0257495, 2012/0157801, 2012/0245447, 2012/0157801, 2012/0323098, and 20130116524, the disclosures of each of which are incorporated herein by reference in their entirety.

Briefly, in vivo electrochemical sensors may be wholly implantable in a user or may be configured so that only a portion is positioned within (internal; e.g., positioned under skin of a subject) a user and another portion outside (external) a user. For example, the sensor may include a first portion positionable above a surface of the skin, and a second portion positioned below the surface of the skin. Such analyte sensors may have any desired configuration.

In some embodiments, in vivo sensors may include an insertion tip positionable below the surface of the skin, e.g., penetrating through the skin and into, e.g., the subcutaneous space, in contact with the user's biological fluid such as interstitial fluid. Contact portions of working electrode, a reference electrode and a counter electrode are positioned on the first portion of the sensor situated above the skin surface. A working electrode, a reference electrode and a counter electrode are positioned at the inserted portion of the sensor.

Traces may be provided from the electrodes at the tip to a contact configured for connection with sensor electronics.

In certain embodiments, the working electrode and counter electrode of the sensor as well as the material and the dielectric layers are provided in a layered configuration or construction. For example, the sensor may include a non-conductive material layer, and a first conductive layer such as conductive polymer, carbon, platinum-carbon, gold, etc., disposed on at least a portion of the non-conductive material layer (as described above). The reagent composition is positioned on the sensing structures of the working electrode. A first insulation layer, such as a first dielectric layer may disposed or layered on at least a portion of the first conductive layer and a second conductive layer may be positioned or stacked on top of at least a portion of the first insulation layer (or dielectric layer). The second conductive layer may provide a reference electrode. A second insulation layer, such as a second dielectric layer may be positioned or layered on at least a portion of the second conductive layer. Further, a third conductive layer may be positioned on at least a portion of the second insulation layer and may provide the counter electrode. Finally, a third insulation layer may be disposed or layered on at least a portion of the third conductive layer. In this manner, the sensor may be layered such that at least a portion of each of the conductive layers is separated by a respective insulation layer (for example, a dielectric layer).

In other embodiments, some or all of the electrodes may be provided in a co-planar manner such that two or more electrodes may be positioned on the same plane (e.g., side-by side (e.g., parallel) or angled relative to each other) on the material. For example, co-planar electrodes may include a suitable spacing therebetween and/or include a dielectric material or insulation material disposed between the conductive layers/electrodes. Furthermore, in certain embodiments one or more of the electrodes may be disposed on opposing sides of the non-conductive material. In such embodiments, electrical contact may be one the same or different sides of the non-conductive material. For example, an electrode may be on a first side and its respective contact may be on a second side, e.g., a trace connecting the electrode and the contact may traverse through the material.

In vivo electrochemical analyte sensors may be insertable into the subcutaneous tissue, vein, artery, or other portion of the body containing fluid. Embodiments of the electrochemical analyte sensors may have membranes configured to have an analyte permeability that is substantially temperature independent may be configured for monitoring the level of the analyte over a time period which may range from seconds, minutes, hours, days, weeks, to months, or longer.

In vivo electrochemical analyte sensors according to certain embodiments may be configured to operate at low oxygen concentration. By low oxygen concentration is meant the concentration of oxygen is 1.5 mg/L or less, such as 1.0 mg/L or less, such as 0.75 mg/L or less, such as 0.6 mg/L or less, such as 0.3 mg/L or less, such as 0.25 mg/L or less, such as 0.15 mg/L or less, such as 0.1 mg/L or less and including 0.05 mg/L or less. In certain instances, sensors according to the present disclosure operate in the complete absence of oxygen (i.e., 0 mg/L).

Methods for Monitoring an Analyte Concentration

Aspects of the present disclosure also include a method for monitoring a level of an analyte in a subject employing one or more of the subject analyte sensors described above. Generally, monitoring the concentration of an analyte in a fluid of the body of a subject includes contacting the monitored fluid with the sensor, generating a sensor signal at the working electrode, and monitoring the concentration of the analyte using the sensor signal. It will be understood that the subject methods may employ any of the analyte sensors described herein. For example, the analyte sensor may include: a working electrode; and a counter electrode where the working electrode includes a non-conductive material; a conductive layer disposed on and in contact with the material and a sensing structure on the conductive layer having an incomplete perimeter around the sensing structure and reagent, such as analyte responsive enzyme, positioned within the boundaries of the sensing structure.

A variety of approaches may be employed to determine the concentration of the analyte. In certain aspects, an electrochemical analyte concentration monitoring approach is used. For example, monitoring the concentration of the analyte using the sensor signal may be performed by coulometric, amperometric, voltammetric, potentiometric, or any other convenient electrochemical detection technique.

If an analyte concentration is successfully determined, it may be displayed, stored, and/or otherwise processed to provide useful information. As demonstrated herein, the methods of the present disclosure are useful in connection with a device that is used to measure or monitor an analyte (e.g., glucose), such as any such device described herein. These methods may also be used in connection with a device that is used to measure or monitor another analyte, including oxygen, carbon dioxide, electrolytes, or other moieties of interest, for example, or any combination thereof, found in a bodily fluid, including subcutaneous e.g. interstitial fluid, dermal fluid, blood or other bodily fluid of interest or any combination thereof.

Methods for using an in vivo electrochemical analyte sensor may include positioning at least a portion of an electrochemical sensor beneath a skin surface of a user, for example, into a site such that subcutaneous fluid, or dermal fluid or blood comes into contact with the sensor (e.g. subcutaneous space, dermal space or blood vessel). The sensor operates to electrolyze an analyte of interest in the biological fluid such that a current is generated between the working electrode and the counter electrode. A value for the current associated with the working electrode is determined. If multiple working electrodes are used, current values from each of the working electrodes may be determined. A microprocessor may be used to collect these periodically determined current values or to further process these values.

For example, in some embodiments, the method includes: positioning at least a portion of an analyte sensor into the skin of the subject and determining a level of an analyte over a period of time from signals generated by the analyte sensor such that determining over a period of time provides for monitoring the level of the analyte in the subject. In certain embodiments, the method further includes attaching an analyte sensor control unit to the skin of the patient; coupling a plurality of conductive contacts of the analyte sensor control unit to a plurality of contact pads of the analyte sensor; collecting data, using the analyte sensor control unit, regarding a level of an analyte from signals generated by the analyte sensor; and transmitting the collected data from the analyte sensor control unit to a receiver unit.

The electrochemical sensor may be positionable in a user for the continuous or periodic monitoring of a level of an analyte in the user's biological fluid. The sensor response may be correlated and/or converted to analyte levels in blood or other fluids. In certain embodiments, an analyte sensor may be positioned in contact with interstitial fluid in the subcutaneous space or dermal space to detect the level of glucose. Analyte sensors may also be insertable into a vein, artery, or other portion of the body containing fluid. Embodiments of the analyte sensors may be configured for monitoring the level of the analyte over a time period which may range from seconds, minutes, hours, days, weeks, to months, or longer.

Future analyte levels may be predicted based on information obtained, e.g., the current analyte level at time zero as well as the rate of change of the analyte.

In some embodiments, the sensor is placed, transcutaneously, for example, into a subcutaneous or dermal site such that subcutaneous fluid of the site comes into contact with the sensor. In other in vivo embodiments, placement of at least a portion of the sensor may be in a blood vessel. The sensor operates to electrolyze an analyte of interest in the subcutaneous fluid such that a current is generated between the working electrode and the counter electrode. A value for the current associated with the working electrode is determined. If multiple working electrodes are used, current values from each of the working electrodes may be determined. A microprocessor may be used to collect these periodically determined current values or to further process these values.

If an analyte concentration is successfully determined, it may be displayed, stored, transmitted, and/or otherwise processed to provide useful information. By way of example, raw signal or analyte concentrations may be used as a basis for determining a rate of change in analyte concentration, which should not change at a rate greater than a predetermined threshold amount. If the rate of change of analyte concentration exceeds the predefined threshold, an indication maybe displayed or otherwise transmitted to indicate this fact.

The sensor electronics unit may continuously or periodically transmit sensor data to the receiver unit,—e.g., as may occur with continuous glucose monitoring systems. The sensor data may be communicated periodically, such as at a certain frequency as data is obtained or after a certain time period of sensor data is stored in memory. For example, sensor electronics coupled to an in vivo positioned sensor may collect the sensor data for a predetermined period of time and transmit the collected data periodically (e.g., every minute, five minutes, or other predetermined period) to an analyte monitoring device that is positioned in range from the sensor electronics.

The sensor data may include a number of samples taken over time and may be digital data that is representative of a continuous signal. For instance, numerous samples of a test subject's glucose level may be taken over time at a predetermined sampling rate and be representative of the continuous change in glucose level of the test subject over that time period.

In other embodiments, the sensor electronics coupled to the in vivo positioned sensor may communicate with the analyte monitoring device in a non-periodic manner and not set to any specific schedule or frequency. For example, the sensor data may be communicated from the sensor electronics to the analyte monitoring device using RFID technology, and communicated whenever the sensor electronics are brought into communication range of the analyte monitoring device. For example, the in vivo positioned sensor may collect sensor data in memory until the analyte monitoring device (e.g., receiver unit) is brought into communication range of the sensor electronics unit—e.g., by the patient or user. When the in vivo positioned sensor is detected by the analyte monitoring device, the device establishes communication with the sensor electronics and uploads the sensor data that has been collected since the last transfer of sensor data, for instance. In this way, the patient does not have to carry the analyte monitoring device at all times, and instead, can upload sensor data when desired by bringing the analyte monitoring device into range of the analyte sensor. In yet other embodiments, a combination of periodic and non-periodic transfers of sensor data may be implemented in certain embodiments. For example, transfers of sensor data may be initiated when brought into communication range o, and then continued on a periodic basis if continued to remain in communication range.

As demonstrated herein, the methods of the present disclosure are useful in connection with a device that is used to measure or monitor a glucose analyte, such as any such device described herein. These methods may also be used in connection with a device that is used to measure or monitor another analyte (e.g., ketones, ketone bodies, HbA1c, and the like), including oxygen, carbon dioxide, proteins, drugs, or another moiety of interest, for example, or any combination thereof, found in bodily fluid, including subcutaneous fluid, dermal fluid (sweat, tears, and the like), interstitial fluid, or other bodily fluid of interest, for example, or any combination thereof. In general, the device is in good contact, such as thorough and substantially continuous contact, with the bodily fluid.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1

Two sensors having sensing structures with fluid barrier perimeters of removed conductive material were made. Conductive material was applied to non-conductive material. The conductive material was then laser ablated to form electrodes as well as the sensing structures.

Figure 9:
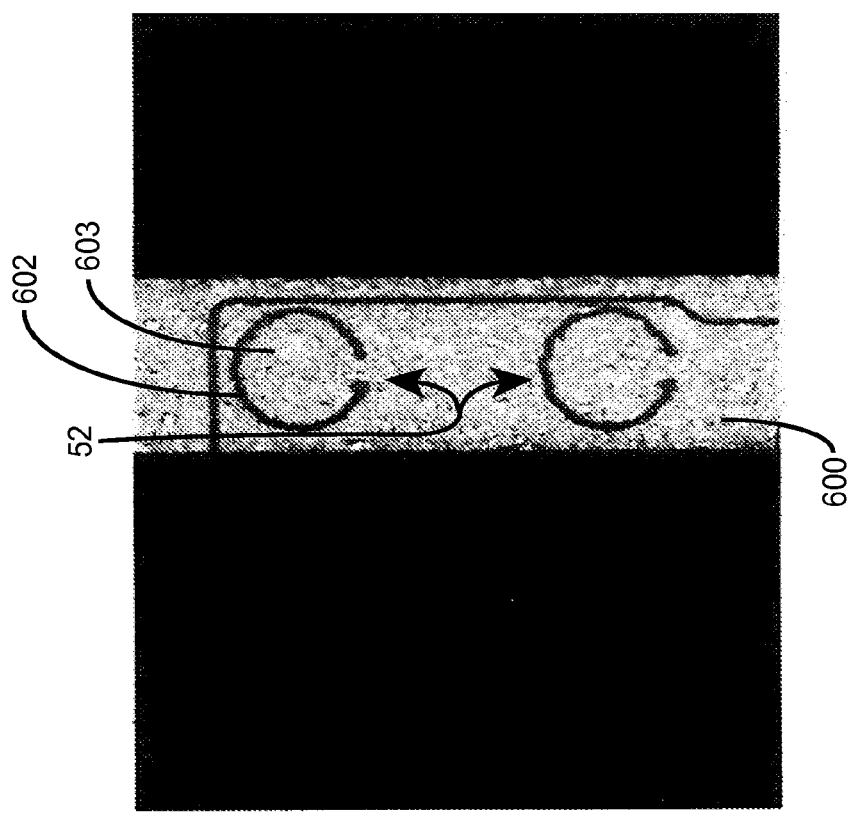
FIG. 9 shows a photograph of an electrode with two regions laser ablated to include circular perimeters on a roughened gold coated electrode substrate.
Figure 10:
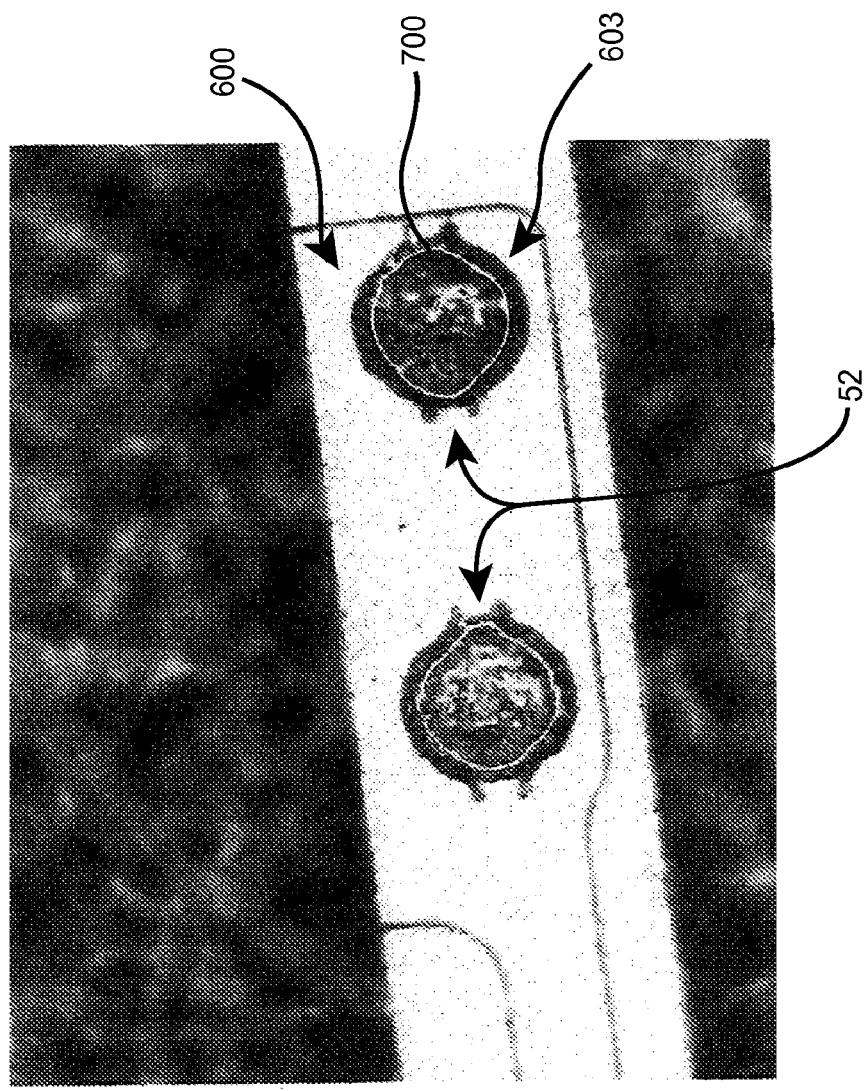
FIG. 10 shows a photograph of the electrode of FIG. 9 having about 20 nL of reagent composition deposited within the boundaries of the sensing structures.

FIG. 9 shows a photograph of an electrode 600 with two sensing structures 52 and each has a respective laser ablated incomplete circular perimeter 602 with an interior 603. A 20 nL (FIG. 10) solution of reagent composition 700 was then deposited within the fluid barrier perimeter 602 of the sensing structures 52 of electrode 600. As illustrated in FIG. 10, the fluid retaining barrier of the electrode 602 restricted the migration of the reagent composition outside of the sensing structures 52 and formed uniformly distributed reagent composition wholly contained within the interior in the sensing structures 52.

Example 2

Figure 11:
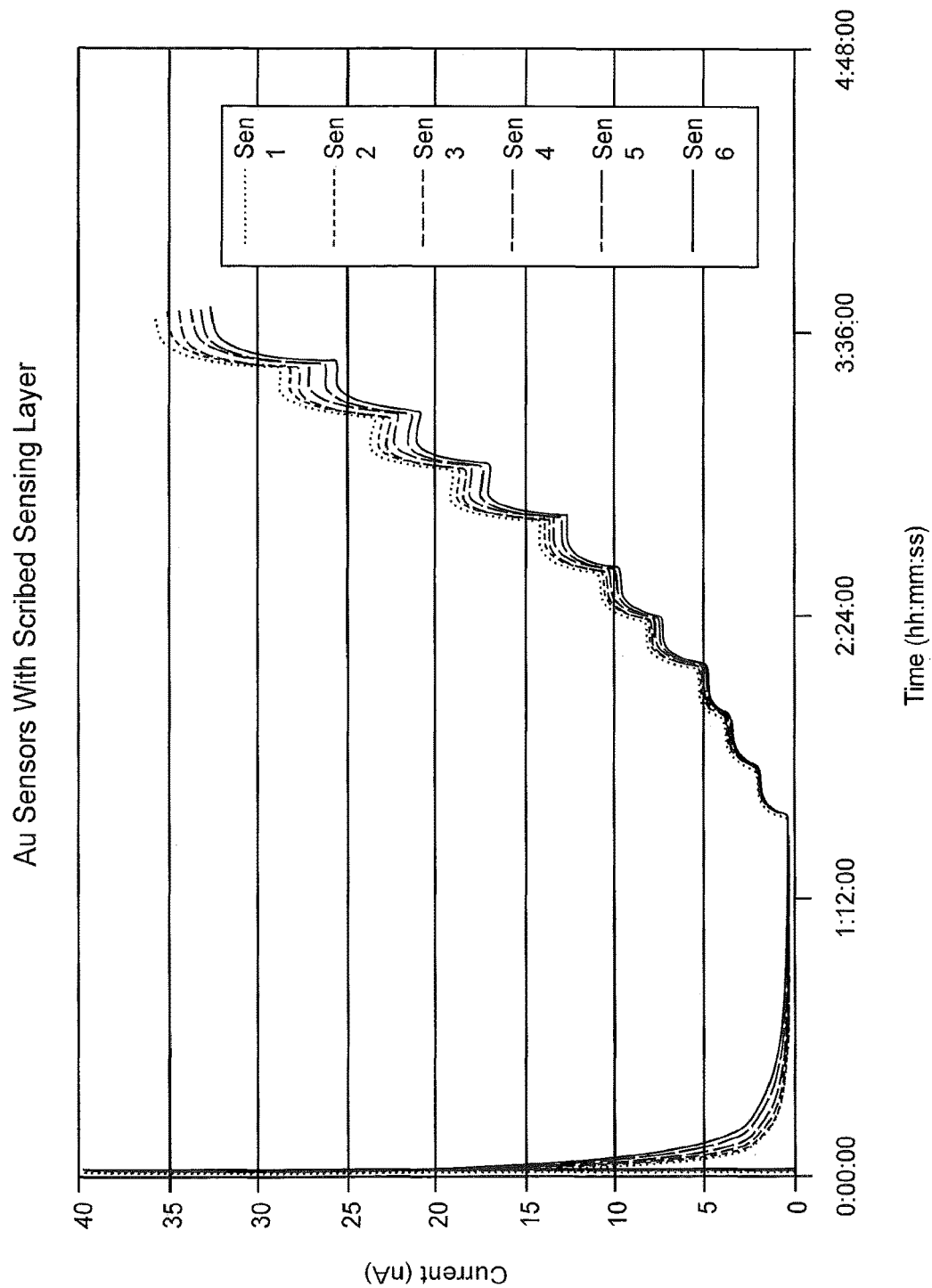
FIG. 11 shows a graph of current (nA) vs. time (hours:minutes:seconds) for six electrochemical sensors configured with a working electrode having sensing structures with ablated incomplete circular perimeters and having reagent composition confined to the area of the sensing structures.

FIG. 11 shows a graph of current (nA) vs. time (hours: minutes:seconds) for six electrochemical sensors configured with a working electrode having sensing structures with reagent composition confined to the area of the sensing structures by ablated incomplete circular perimeters formed as described in Example 1. The data of the sensors shown in FIG. 11 had a coefficient of sensitivity of approximately 3%.

What is claimed is:

1. An in vivo analyte sensor, comprising:
an electrode comprising a conductive material; and
a plurality of sensing structures on the electrode, wherein each of the plurality of sensing structures comprises:
a region of the conductive material having a fluid barrier arranged along at least a portion of a perimeter of the region, and
a reagent composition disposed on the region,
wherein the fluid barrier comprises a build-up of material on a surface of the electrode.

2. The analyte sensor of claim 1, wherein the fluid barrier extends along at least 50% of the perimeter of a sensing structure of the plurality of sensing structures.

3. The analyte sensor of claim 1, wherein the fluid barrier extends along an entirety of the perimeter of a sensing structure of the plurality of sensing structures.

4. The analyte sensor of claim 1, wherein the fluid barrier is discontinuous about the perimeter of a sensing structure of the plurality of sensing structures.

5. The analyte sensor of claim 1, wherein the conductive material is arranged on a non-conductive material.

6. The analyte sensor of claim 1, wherein the reagent composition comprises an analyte-responsive enzyme.

7. The analyte sensor of claim 1, wherein the reagent composition is uniformly distributed on a sensing structure of the plurality of sensing structures.

8. The analyte sensor of claim 1, wherein the electrode is a working electrode, and wherein the analyte sensor further comprises a counter electrode.

9. The analyte sensor of claim 1, wherein the plurality of sensing structures comprises a first sensing structure spaced from a second sensing structure by an inter-sensing area.

10. The analyte sensor of claim 9, wherein the inter-sensing area does not include the reagent composition.

11. A method, comprising:
determining a level of an analyte in a bodily fluid from signals generated by an in vivo analyte sensor, wherein the in vivo analyte sensor comprises:
an electrode comprising a conductive material and a plurality of sensing structures on the electrode, wherein each of the plurality of sensing structures comprises:
a region of the conductive material having a fluid barrier arranged along at least a portion of a perimeter of the region, and
a reagent composition disposed on the region,
wherein the fluid barrier comprises a build-up of material on a surface of the electrode.

12. The method of claim 11, further comprising placing the analyte sensor in contact with the bodily fluid under a skin surface of a user.

13. The method of claim 11, wherein the analyte sensor is factory calibrated.

14. The method of claim 11, wherein the reagent composition comprises an analyte responsive enzyme.

15. A method of manufacturing an electrode for an in vivo analyte sensor, the method comprising:
forming a plurality of sensing structures on a conductive material of the electrode, wherein forming each of the plurality of sensing structure comprises:
forming a fluid barrier at least partially surrounding a region of a conductive material of an electrode; and
depositing a reagent composition on the region at least partially surrounded by the fluid barrier,
wherein forming the fluid barrier comprises depositing a material on a surface of the conductive material of the electrode.

16. The method of claim 15, further comprising arranging the conductive material on a non-conductive material.

17. The method of claim 16, further comprising conditioning a surface of the non-conductive material prior to arranging the conductive material on the non-conductive material.

18. The method of claim 15, wherein depositing the reagent composition on the region is performed prior to forming the fluid barrier at least partially surrounding the region.

* * * * *